US00PP25514P2

(12) United States Plant Patent
Hanna et al.

(10) Patent No.: US PP25,514 P2
(45) Date of Patent: May 5, 2015

(54) GRASS 'TIFT 11'

(50) Latin Name: ***Pennisetum* hybrid**
Varietal Denomination: Tift 11

(71) Applicant: University of Georgia Research Foundation, Inc., Athens, GA (US)

(72) Inventors: Wayne W. Hanna, Chula, GA (US); S. Kristine Braman, Griffin, GA (US); Brian M. Schwartz, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 153 days.

(21) Appl. No.: 13/986,880

(22) Filed: Jun. 13, 2013

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para
(74) *Attorney, Agent, or Firm* — Klarquist Sparkman, LLP

(57) ABSTRACT

The new variety *Pennisetum* 'Tift 11' is provided. The new and distinct variety has high ornamental value, cold tolerance for short periods of time, and disease resistance. The asexually reproduced variety is reliably propagated vegetatively.

1 Drawing Sheet

Latin name of the genus and species of the plant claimed: 'Tift 11' is a tri-specific ornamental *Pennisetum* hybrid of the genus and species *Pennisetum purpureum*×[*Pennisetum glaucum*×(*Pennisetum purpureum*×*Pennisetum squamulatum*)].

Variety denomination: The new *Pennisetum* claimed is of the variety denominated 'Tift 11'.

BACKGROUND OF THE INVENTION

The present invention relates to a new and distinct cultivar of *Pennisetum* herein referred to as 'Tift 11'.

The new *Pennisetum* 'Tift 11' is a product of a planned breeding program conducted by the Inventors in Tifton, Ga. The objective of the *Pennisetum* breeding program is to create new plant cultivars with improved commercial qualities. This cultivar is commercially important for its superior ornamental value. These and other qualities are enumerated herein.

Pedigree and history: In 2003, red tetraploid (2n=4x=28) pearl millet (unpatented *Pennisetum glaucum*; designated '04-94') was crossed with SC 1125-2 [a Merkeron napiergrass (unpatented *Pennisetum purpureum;* 2n=4x=28) that had been crossed with PS 262 (unpatented *Pennisetum squamulatum;* 2n=8x=56)]. One vigorous plant, from the 04-94/SC 1125-2 cross, designated '04-26-1', was selected in 2004. In 2004, 'Princess' napiergrass (U.S. Plant Pat. No. 17,728; 2n=4x=28, female parent) was pollinated with '04-26-1' (unpatented; male parent). The new variety 'Tift 11' was the eleventh plant selected in 2005 from the 2004 cross. The new variety 'Tift 11' has been tested since 2005.

Asexual reproduction of the new *Pennisetum* 'Tift 11' by vegetative propagation (single stem propagules) in a controlled environment in Tifton, Blairsville and Griffin, Ga. since 2005, has shown that the unique features of this new *Pennisetum* hybrid are stable and reproduced true to type in successive generations.

SUMMARY OF THE INVENTION

The following traits have been repeatedly observed and represent the characteristics of a new variety *Pennisetum*, 'Tift 11'. The new variety 'Tift 11' has not been observed under all possible environmental conditions. The phenotype may vary somewhat with variations in, for example, temperature, day-length, light intensity, soil types, and water and fertility levels without, however, any variance in genotype.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following traits have been repeatedly observed in Tifton, Blairsville, and Griffin, Ga., and are determined to be the unique characteristics of the new variety 'Tift 11':

1. 'Tift 11' reaches a height of about 1.2 meters, and a spread of about 1.5 meters.
2. 'Tift 11' exhibits a vigorous growth habit.
3. 'Tift 11' is pollen and seed sterile.

The new variety *Pennisetum* 'Tift 11' can be compared to its parents, 'Princess' and '04-26-01', and to 'Princess Caroline' (aka 'Tift 17') (U.S. Plant Pat. No. 21,464).

Plants of the new *Pennisetum* 'Tift 11' differ from its female parent 'Princess' in the following characteristics:

1. The new variety 'Tift 11' is taller, has longer leaves, and does not have the mottled, grey-purple/green color compared to 'Princess'.

Plants of the new *Pennisetum* 'Tift 11' differ from its male parent '04-26-1' in the following characteristics:

1. The new variety 'Tift 11' is shorter, has wider leaves, and slightly different from '04-26-1' in adaxial leaf color. The new variety 'Tift 11' is about Greyed-purple RHS 186C, whereas '04-26-1' is about mottled Greyed-purple/green RHS 183B/138A.
2. The new variety 'Tift 11' has a different midrib color than the midrib color of '04-26-1'. The new variety 'Tift 11' has a midrib color that is about Greyed-purple RHS 187B, while '04-26-1' has a midrib color that is about Red-purple RHS 61C.

Plants of the new *Pennisetum* 'Tift 11' differ from its sister hybrid 'Princess Caroline' in the following characteristics:

1. The new variety 'Tift 11' is significantly taller than 'Princess Caroline'.
2. Culm-leaf angle is significantly smaller for 'Tift 11' compared to the culm-leaf angle of 'Princess Caroline'.

The following observations, measurements, and values describe plants grown in Tifton, Blairsville, or Griffin, Ga. In Tables 1-5, the least significant difference (LSD) is set at P≤0.05 probability level. Growth days were included in ratings. Plants were spaced at 2 meter centers. All data are from plants established as single stem propagules in mid-May and rated in September through October, except the data from 2010 and 2011, in which the plants had been overwintered at Tifton, Ga.

The new variety 'Tift 11' was significantly taller than 'Princess Caroline' in six of eight tests at Tifton, Griffin, and Blairsville, Ga. (Table 1). The canopy diameter was observed to be similar between 'Tift 11' and 'Princess Caroline' in five of eight tests and 'Tift 11' was significantly wider than 'Princess Caroline' in three of eight tests (Table 2). 'Tift 11' has an attractive reddish/purple color and was equal to 'Princess Caroline' in seven of eight tests (Table 3). The new variety 'Tift 11', similarly to 'Princess Caroline', is not disease-susceptible to *Helminthosporium* leaf spot, whereas 'Princess' is susceptible to this disease (Table 4). Leaves of 'Tift 11' are significantly shorter, narrower, and have less leaf area than leaves of 'Princess Caroline' (Table 5). The narrow leaves give this cultivar a unique attractive appearance. Culm-leaf angle was significantly smaller for 'Tift 11' as compared to the culm-leaf angle for 'Princess Caroline' (Table 5) which gives 'Tift 11' a lesser upright leaf structure.

TABLE 1

Plant heights (cm) of two ornamental *Pennisetum* grasses planted at three locations in Georgia.

| | Tifton | | | Blairsville | | | Griffin | |
|---|---|---|---|---|---|---|---|---|
| | 2009 | 2010 | 2011 | 2009 | 2010 | 2011 | 2009 | 2010 |
| Growth days | 153 d | 150 d | 183 d | 144 d | 145 d | 160 d | 138 d | 124 d |
| 'Tift 11' | 102 | 125 | 123 | 121 | 124 | 141 | 162 | 142 |
| 'Princess Caroline' | 95 | 107 | 85 | 107 | 78 | 115 | 137 | 108 |
| LSD | 7 | 15 | 14 | NS | 15 | 25 | 21 | 24 |

In Table 1, plant heights were measured from ground level to top of plant canopy. All height measurements are in cm. At Tifton, Ga., 'Tift 11' and 'Princess Caroline' were planted on May 9, 2009, May 9, 2010, and May 12, 2011, with measurements taken on Oct. 12, 2009, Sep. 29, 2010, and Oct. 18, 2011. At Blairsville, Ga., 'Tift 11' and 'Princess Caroline' were planted on May 14, 2009, May 11, 2010, and May 1, 2011, with measurements made on Oct. 8, 2009, Oct. 6, 2010 and Oct. 10, 2011, respectively. At Griffin, Ga., 'Tift 11' and 'Princess Caroline' were planted on May 14, 2009 and May 14, 2010, with measurements taken on Oct. 2, 2009 and Sep. 10, 2010.

TABLE 2

Canopy diameter (cm) of individual plant of two ornamental *Pennisetum* grasses planted at three locations in Georgia. Plants were spaced on two meter centers.

| | Tifton | | | Blairsville | | | Griffin | |
|---|---|---|---|---|---|---|---|---|
| | 2009 | 2010 | 2011 | 2009 | 2010 | 2011 | 2009 | 2010 |
| Growth days | 153 d | 150 d | 183 d | 144 d | 145 d | 160 d | 138 d | 124 d |
| 'Tift 11' | 150 | 129 | 147 | 148 | 165 | 165 | 206 | 165 |
| 'Princess Caroline' | 135 | 129 | 131 | 152 | 146 | 162 | 163 | 155 |
| LSD | 7 | NS | 10 | NS | 15 | NS | 28 | NS |

Plant canopy measurements, as shown in Table 2, represent the average diameters measured at the estimated widest and narrowest portions of a single plant canopy. Measurements are in cm. At Tifton, Ga., 'Tift 11' and 'Princess Caroline' were planted on May 9, 2009, May 9, 2010, and May 12, 2011, with measurements taken on Oct. 12, 2009, Sep. 29, 2010, and Oct. 18, 2011. At Blairsville, Ga., 'Tift 11' and 'Princess Caroline' were planted on May 14, 2009, May 11, 2010, and May 1, 2011, with measurements made on Oct. 8, 2009, Oct. 6, 2010, and Oct. 10, 2011. At Griffin, Ga., 'Tift 11' and 'Princess Caroline' were planted on May 14, 2009 and May 14, 2010, with measurements taken on Oct. 2, 2009 and Sep. 10, 2010.

TABLE 3

Color ratings on individual plants of two ornamental *Pennisetum* grasses planted at three locations in Georgia. Plants were spaced on two meter centers.

| | Tifton | | | Blairsville | | | Griffin | |
|---|---|---|---|---|---|---|---|---|
| | 2009 | 2010 | 2011 | 2009 | 2010 | 2011 | 2009 | 2010 |
| Growth days | 153 d | 150 d | 183 d | 144 d | 145 d | 160 d | 138 d | 124 d |
| 'Tift 11' | 8.0 | 8.0 | 7.8 | 7.6 | 8.0 | 8.0 | 7.6 | 8.0 |
| 'Princess Caroline' | 8.0 | 7.1 | 7.6 | 7.3 | 7.6 | 7.6 | 8.0 | 8.0 |
| LSD | NS | 0.5 | NS | NS | NS | NS | NS | NS |

Color ratings are measured on a scale of 1 to 9, where 1 represents green and 9 represents dark purple/red. At Tifton, Ga., 'Tift 11' and 'Princess Caroline' were planted May 9, 2009, May 9, 2010, and May 12, 2011, with measurements taken on Oct. 12, 2009, Sep. 29, 2010, and Oct. 18, 2011. At Blairsville, Ga., 'Tift 11' and 'Princess Caroline' were planted on May 14, 2009, May 11, 2010, and May 1, 2011, with measurements taken on Oct. 8, 2009, Oct. 6, 2010, and Oct. 10, 2011. At Griffin, Ga., 'Tift 11' and 'Princess Caroline' were planted on May 14, 2009 and May 14, 2010, with measurements taken Oct. 2, 2009 and Sep. 10, 2010.

TABLE 4

*Helminthosporium* leaf spot ratings on three ornamental *Pennisetum* grasses planted at three locations in Georgia.

| | Tifton | | | Blairsville | | Griffin |
|---|---|---|---|---|---|---|
| | 2009 | 2010 | 2011 | 2010 | 2011 | 2009 |
| Growth days | 153 d | 150 d | 183 d | 145 d | 160 d | 138 d |
| 'Tift 11' | 1.0 | 1.0 | 1.0 | 1.0 | 1.0 | 1.0 |
| 'Princess Caroline' | 1.0 | 1.0 | 1.0 | 1.0 | 1.0 | 1.0 |
| 'Princess' | 5.2 | 6.6 | 8.0 | 5.0 | 7.6 | 6.6 |
| LSD | 0.4 | 0.1 | 0.0 | 1.2 | 0.2 | 0.6 |

Disease ratings in Table 9 are defined as follows: 1=No disease, 2=1-20%, 3=21-30%, 4=31-40%, 5=41-50%, 6=51-60%, 7=61-70%, 8=71-80%, 9=>80% leaves infected. Symptoms occur in the field during late August and September. At Tifton, Ga., 'Tift 11' and 'Princess Caroline' were planted on May 9, 2009, May 9, 2010, and May 12, 2011, with measurements taken on Oct. 12, 2009, Sep. 29, 2010, and Oct. 18, 2011. At Blairsville, Ga., 'Tift 11' and 'Princess Caroline' were planted on May 14, 2009, May 11, 2010, and May 1, 2011, with measurements taken on Oct. 8, 2009, Oct. 6, 2010, and Oct. 10, 2011. At Griffin, Ga., 'Tift 11' and 'Princess Caroline' were planted on May 14, 2009, with measurements taken on Oct. 2, 2009.

TABLE 5

Leaf characteristics of individual plants of two ornamental *Pennisetum* grasses planted at Tifton, Georgia in 2009. Plants were spaced on two meter centers.

| Entry | Leaf Length(cm) | Leaf Width(mm) | Leaf Area($cm^2$) | Leaf Angle Culm:Leaf-degrees |
|---|---|---|---|---|
| 'Tift 11' | 65 | 29 | 128 | 10 |
| 'Princess Caroline' | 72 | 37 | 179 | 18 |
| LSD | 6 | 4 | 33 | 2 |

The leaf length was measured in cm from the leaf collar to the leaf tip of the latest fully extended leaf. The leaf width was measured in mm in the center of the latest fully extended leaf. The leaf area was measured in $cm^2$ using a LiCor area meter using the mean of three leaves per replication. The measured leaf angle was the angle observed between the adaxial leaf angle surface and the culm at the leaf collar on the last fully extended leaf and was measured in degrees. At Tifton, Ga., 'Tift 11' was planted on May 9, 2009, with measurements taken on Sep. 12, 2009.

TABLE 6

Summary of morphological characteristics of two *Pennisetum* grasses.

| Trait | 'Princess Caroline' | 'Tift 11' |
|---|---|---|
| Mature plant height | 95-137 cm | 102-162 cm |
| Diameter of plant canopy | 129-163 cm | 129-206 cm |

TABLE 6-continued

Summary of morphological characteristics of two *Pennisetum* grasses.

| Trait | 'Princess Caroline' | 'Tift 11' |
|---|---|---|
| Leaf width | 37 mm | 29 mm |
| Leaf length | 72 cm | 65 cm |
| Leaf Area-$cm^2$ | 179 | 128 |
| Leaf Angle (Culm:Leaf) | 18 degrees | 10 degrees |
| Adaxial leaf surface trichomes | None | Few, 1 mm along both sides of the midrib |
| Abaxial leaf surface trichomes | None | None |
| Leaf blade margin trichome length | <0.1 m | Slight remnant less than 0.1 mm |
| Leaf collar trichome length | 3 mm | 4 mm |
| Leaf blade edge at collar Trichome | 6 mm long for 6 cm from collar | Moderate, 5 mm long for 6 cm from collar |
| Sheath trichomes | 2 mm long for 2 cm from collar | None |
| Adaxial leaf color | Greyed-purple 187D | Greyed-purple 186C |
| Abaxial leaf color | Greyed-purple 187D | Greyed-purple 186C |
| Midrib color | Greyed-purple 187D | Greyed-purple 187B |
| Inflorescence on Oct. 20, 2008 | None | None |
| Inflorescences on Dec. 21, 2009 | None | None |
| *Helminthosporium* leaf spot on mature plants | None | None |

In summary, 'Tift 11' is similar to 'Princess Caroline' in canopy diameter, color, and disease resistance. 'Tift 11' is taller and has shorter and narrower leaves and a smaller culm-leaf angle than 'Princess Caroline'.

BRIEF DESCRIPTION OF THE FIGURES

The accompanying colored photographs illustrate the overall appearance and distinct characteristics of the new variety of *Pennisetum* 'Tift 11'. The colors in the photographs are as close as possible with the photographic and printing technology utilized.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

FIG. 1 is a photograph of the new variety *Pennisetum* 'Tift 11'.

BOTANICAL DESCRIPTION

The new variety 'Tift 11' is a perennial at Tifton, Ga. (USDA Zone 8a). The new variety 'Tift 11' survived at approximately −6° C. for one night and 21 nights below 0° C. in the field during the 2009/2010 winter at Tifton. It has survived the winter temperatures (below 0° C. for 60 days and a low temperature of −8° C. during 2009/2010) in Griffin, Ga. (USDA Zone 7b). It did not survive the winter temperatures (lows of −15° C. in 2009/2010 and 2010/2011) in the mountains of Blairsville, Ga. (USDA Zone 6b). Because of its vigor, 'Tift 11' can effectively be used as an annual where it will not survive freezing temperatures in the winter.

All data are from plants established as single stem propagules in mid-May, and rated in September through October, except the 2010 and 2011 data are from plants that over-wintered at Tifton. Plants were spaced at 2 meter centers.

Plant:

*Mature plant height*.—Approximately 102-162 cm.

*Diameter of plant canopy*.—Approximately 129-206 cm.

Leaf:

*Leaf width*.—Approximately 29 mm.

*Leaf length*.—Approximately 65 mm.

*Adaxial leaf surface trichomes*.—Few, 1 mm along both sides of the midrib.

*Abaxial leaf surface trichomes*.—None.

*Leaf blade margin trichome length*.—Slight, remnant less than 0.1 mm.

*Leaf collar trichome length*.—4 mm.

*Leaf blade edge at collar trichome*.—Moderate, 5 mm long for 6 cm from collar.

*Sheath trichomes*.—None.

*Adaxial leaf color*.—About Greyed-purple RHS 186C.

*Abaxial leaf color*.—About Greyed-purple RHS 186C.

*Midrib color*.—About Greyed-purple RHS 187B.

*Helminthosporium leaf spot on mature plants*.—None.

*Inflorescence*.—No pollen or seed has been observed on plants flowering in the greenhouse during the winter (short days).

What is claimed is:

1. A new and distinct variety of the *Pennisetum* plant named 'Tift 11', substantially as illustrated and described herein.

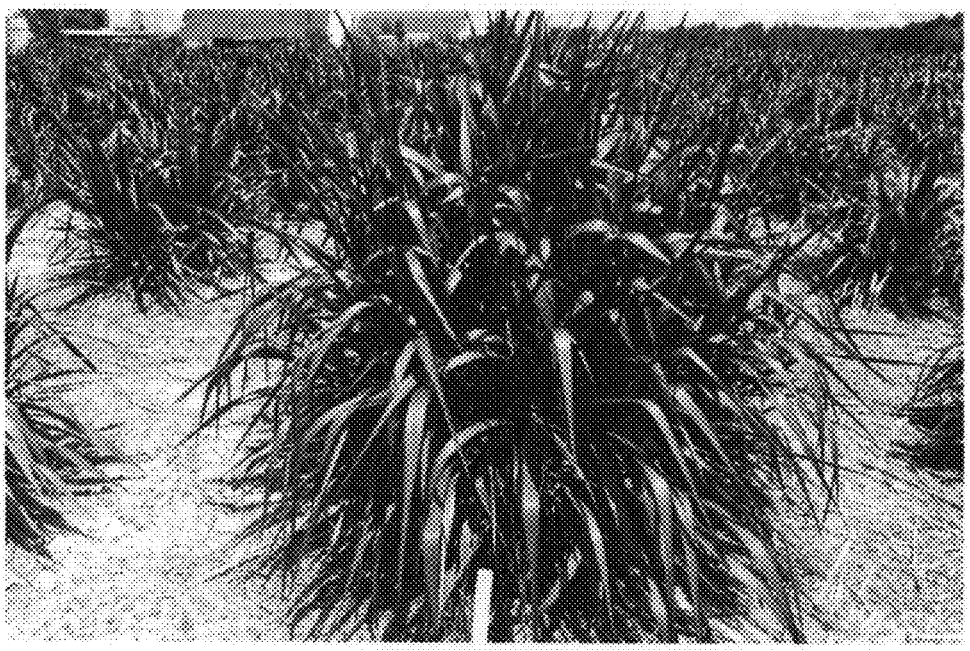

* * * * *